United States Patent [19]

Smith

[11] Patent Number: 4,591,566

[45] Date of Patent: May 27, 1986

[54] BIOLOGICAL INDICATOR PROBE FOR STEAM STERILIZING SYSTEMS

[75] Inventor: William B. Smith, Bloomington, Ill.

[73] Assignee: Bio-Environmental Systems, Inc., Champaign, Ill.

[21] Appl. No.: 555,123

[22] Filed: Nov. 25, 1983

[51] Int. Cl.⁴ ............ C12M 1/34; C12M 1/00; C12M 1/24; C12Q 1/22

[52] U.S. Cl. .................... 435/291; 435/31; 435/287; 435/296; 206/306; 374/157; 374/178

[58] Field of Search ............ 435/31, 287, 291, 296, 435/290; 374/157, 178, 208, 179; 206/306, 540

[56] References Cited

U.S. PATENT DOCUMENTS

| | | | |
|---|---|---|---|
| 533,862 | 2/1895 | Brabrook | 206/540 X |
| 3,031,888 | 5/1962 | Wilhelm | 374/179 X |
| 3,846,242 | 11/1974 | Ernst | 435/31 |
| 3,862,574 | 1/1975 | Antoine et al. | 374/179 |
| 3,871,522 | 3/1975 | Feldman | 206/540 |
| 3,878,049 | 4/1975 | Tannenbaum et al. | 435/291 X |
| 3,948,727 | 4/1976 | Steiger | 435/31 |
| 3,960,670 | 6/1976 | Pflug | 435/31 |
| 4,174,631 | 11/1979 | Hammerslag | 374/179 |
| 4,304,869 | 12/1981 | Dyke | 435/31 X |
| 4,378,885 | 4/1983 | Leopoldi et al. | 206/540 |

FOREIGN PATENT DOCUMENTS

3146346 6/1983 Fed. Rep. of Germany ...... 435/290

*Primary Examiner*—Robert J. Warden
*Assistant Examiner*—Randall E. Deck
*Attorney, Agent, or Firm*—Neal J. Mosely

[57] ABSTRACT

A system is disclosed for monitoring sterilization of biologically contaminated material from hospitals and the like. An autoclave sterilization unit heats biologically contaminated materials with steam for a time sufficient to kill the contaminants therein. A biological indicator probe provides for inserting a test vial into the central portion of the materials being treated. After sterilization, the probe is removed and the test vial is cultured to determine whether the spores of the *Bacillus stearothermophilus*, or the like (e.g. Bacillus sp.) present are still viable. If the test vial has been completely inactivated, it is an indication that decontamination of the other materials in the autoclave is complete. The test probe comprises a rod of heat resistant material having an end chamber closable by a rotatable sleeve. In a position aligning window openings in the chamber and in the sleeve, the test vial may be inserted. Rotation of the sleeve locks the test vial in place. The handle portion of the probe may have a laterally extending recess containing a thermocouple with wires extending out through the rod via a plug or connector insert for connection to an external temperature gauge for directly monitoring temperature of the material being sterilized while the test vial is being exposed to the high temperature steam. The probe can also be used in ethylene oxide sterilization and the like.

21 Claims, 4 Drawing Figures

BIOLOGICAL INDICATOR PROBE FOR STEAM STERILIZING SYSTEMS

BACKGROUND OF THE INVENTION

1. Field of the Invention

This invention relates to new and useful improvements in sterilization systems for biologically contaminated materials in hospitals and the like, and more particularly to a biological indicator probe for use in such sterilization systems.

2. Brief Description of the Prior Art

It is common practice in hospitals, and similar facilities, to provide for the sterilization of biologically contaminated materials by subjecting them to high temperature steam. The exposure of bed sheets, bandages, absorbent cotton, sponges, etc., which have been contaminated with infectious agents, through high temperature steam has been used for inactivating the infectious agents. In the past, however, there has been no control of the sterilization process and there has been no convenient means for monitoring the materials to determine whether the sterilization process is complete.

Forg U.S. Pat. No. 2,904,474 discloses sample specimens for use in a biological sterilization process.

Tannenbaum et al U.S. Pat. No. 3,878,049 discloses a temperature recorder mechanism for measuring a change in temperature evolved by reaction of a substrate with a microorganism.

Hesse et al U.S. Pat. No. 4,336,329 discloses a control mechanism for a treatment chamber enclosing biological materials.

SUMMARY OF THE INVENTION

One of the objects of this invention is to provide a new and improved system for sterilization of biologically contaminated materials.

Another object of this invention is to provide a new and improved sterilization monitoring system for biologically contaminated materials having a probe for positioning a biological test vial in the materials during treatment.

Still another object of this invention is to provide a new and improved sterilization monitoring system having a probe for positioning a biological test vial in the materials being treated and including a thermocouple or other temperature measuring means for monitoring the temperature in the material being treated.

Another object of this invention is to provide a new and improved biological indicator probe formed of a heat resistant material having a chamber for supporting a test vial therein for positioning in biologically contaminated materials to be sterilized by high temperature steam.

Still another object of this invention is to provide a new and improved biological test probe consisting of a rod or tube of heat resistant plastic having a removable probe chamber element at its end for containing a test vial of biological material and having a thermocouple supported adjacent to the test vial with wires connectable outside the sterilization apparatus for measurement of temperature in the mass of material being sterilized.

Other objects of this invention will become apparent from time to time throughout the specification and claims as hereinafter related.

These objects and other objects of the invention are accomplished by a system for monitoring sterilization of biologically contaminated material from hospitals and the like. An autoclave sterilization unit heats biologically contaminated materials with steam for a time sufficient to kill the contaminants therein. A biological indicator probe provides for inserting a test vial into the central portion of the materials being treated. After sterilization, the probe is removed and the test vial is cultured to determine whether the spores of the *Bacillus stearothermophilus*, or the like (e.g. Bacillus sp.) present are still viable. If the test vial has been completely inactivated, it is an indication that decontamination of the other materials in the autoclave is complete. The test probe comprises a rod of heat resistant material having an end chamber closable by a rotatable sleeve. In a position aligning window openings in the chamber and in the sleeve, the test vial may be inserted. Rotation of the sleeve locks the test vial in place. The handle portion of the probe may have a laterally extending recess containing a thermocouple with wires extending out through the rod via a plug or connector insert for connection to an external temperature gauge for directly monitoring temperature of the material being sterilized while the test vial is being exposed to the high temperature steam.

DESCRIPTION OF A PREFERRED EMBODIMENT

Figures 1, 2, 3, 4:
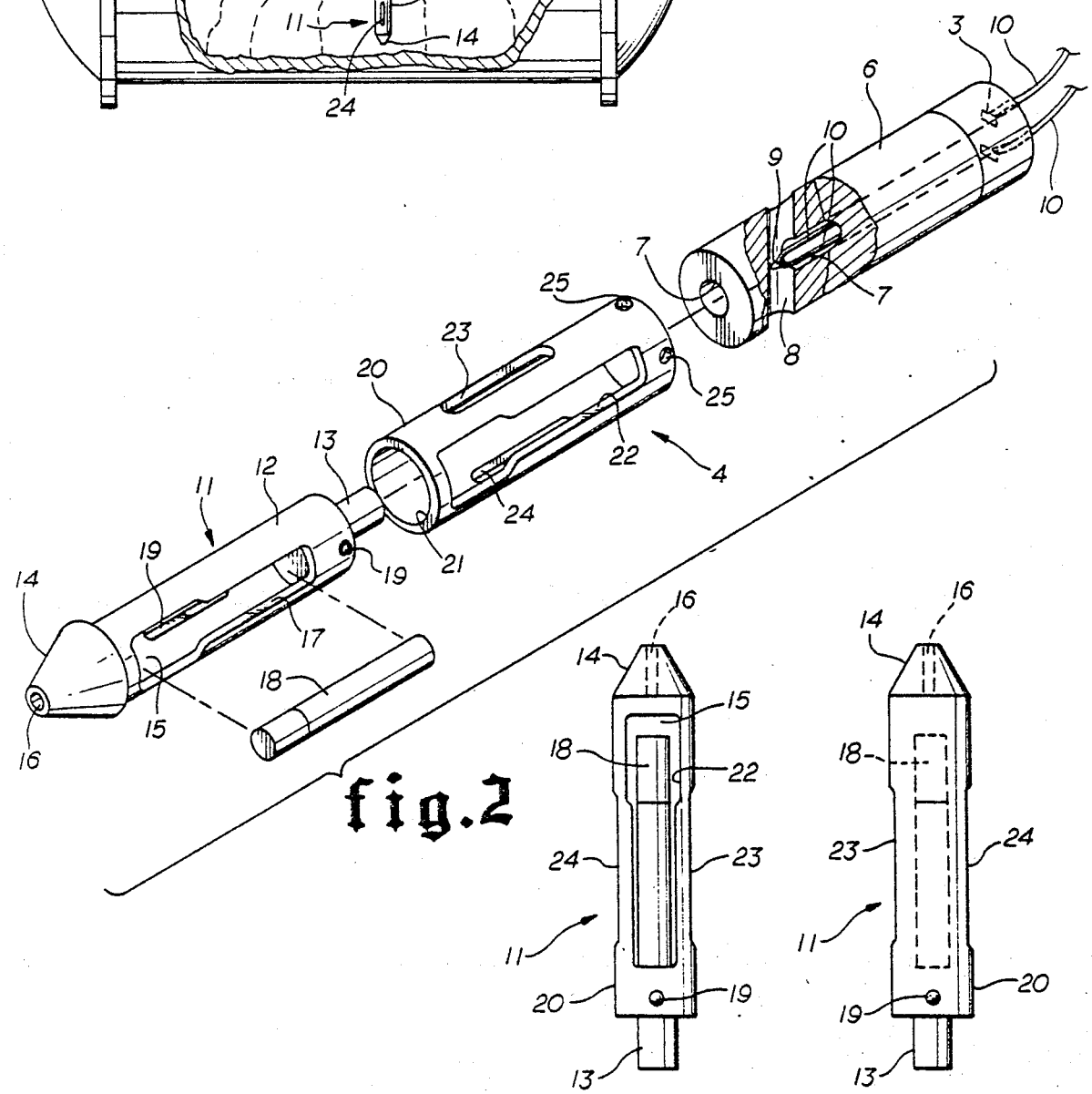
FIG. 1 is a view in broken section of a sterilization autoclave utilizing a biological test probe comprising a preferred embodiment of this invention.
FIG. 2 is an exploded view of the test probe comprising a preferred embodiment of this invention.
FIG. 3 is a detail view of the end of the test probe with a test specimen in place and the test chamber open.
FIG. 4 is a detail view of the end of the test probe with a test specimen in place and the test chamber closed.

Referring to the drawings, and more particularly to FIG. 1, there is shown a somewhat schematic view of an autoclave 1 for treating biologically contaminated materials from hospitals and the like. Autoclave 1 has an opening sealed by a door 2 for insertion of the material to be treated. A mass of biologically contaminated materials 5 is positioned in the sterilizing or sterilization autoclave 1 for treatment.

The contaminated materials may be of any type, usually consist of bloody and or infectious bandages, swabs, sponges, clothing, bed clothing, etc. The infectious waste materials are usually placed in bags for treatment in the autoclave. Items to be sterilized for re-use are usually wrapped in paper or cloth. The autoclave is brought to a sufficiently high temperature for the introduction of pressurized, high temperature steam to heat the contaminated materials to a temperature sufficient to destroy the biological agents present.

Biological indicator probe 4 may be inserted into one of the bags of infectious material being treated or may be inserted between or among the bags or packages so that it is subjected to the same high temperature, high pressure steam that is used for treating the biologically contaminated materials.

In FIGS. 2-4, there are shown views of the biological indicator probe 4 and of the end chamber portion in which the biological test vial is positioned. FIG. 2 is an exploded view of the biological indicator probe 4. FIGS. 3 and 4 are views of the end portion of the biological indicator probe showing the test vial in position in the probe chamber and showing the closure sleeve in an open and a closed position.

In FIG. 2, the biological indicator probe 4 is shown in an exploded view in which it is seen that the probe has a handle portion comprising an elongated hollow rod 6 with a longitudinally extending interior passage 7. In some cases, a solid rod may be used. The rod 6 is of a heat resistant material. Rod 6 is preferably molded from a heat resistant (exceeding 300° F.) thermoplastic (e.g. polysulfone) or thermosetting (e.g. epoxy) resin. It is possible to use a metal, such as stainless steel for the rod, but metals are not preferred.

The handle portion of rod 6 is usually provided with an aperture or opening 8 which extends laterally to and intersects the longitudinally extending passage 7. A thermocouple 9 is positioned in the recess or opening 7 and extending into opening 8 where it is exposed directly to the steam used for sterilization. The thermocouple 10 has wires 10 extending through passage 7 to the end of probe 4 and connected to a plug or connector 3. Thermocouple plug or connector 3 is connectable to an exterior temperature indicator gauge (not shown) for indication of the temperature sensed by thermocouple 9.

Biological indicator probe 4 has a removable end portion or test probe element 11 which is formed of the same material, i.e. polysulfone resin, or the like, as the rod 6. End portion 11 has a cylindrical portion 12 with a smaller cylindrical extension 13 which is sized to fit tightly in the open end of passage 7 on the end of rod 6. End portion 11 has a conical tip portion 14 which is slightly larger in diameter than the main conical portion 12. End portion 11 has an internal pocket or chamber 15. A passage or opening 16 extends from the end of conical tip 14 into pocket or chamber 15. Chamber 15 has an enlarged opening 17 on one side which is of a size sufficient to receive a cylindrical test vial 18. A window or opening 19 is provided on the opposite side of chamber or pocket 15. At the base end of end member 11, there is provided a small peg or boss or abutment 19 for locating the closure sleeve accurately on the probe chamber element.

A sleeve member 20 is provided to fit over test probe element 11 and against the back face of end tip portion 14. Sleeve member 20 is also formed of a heat resistant nonmetallic material, i.e. polysulfone resin or the like. Sleeve member 20 has a cylindrical interior opening 21 having substantially the same diameter as the outside diameter of cylindrical portion 12 of the probe element. Sleeve 20 is therefore sized for a sliding rotatable fit.

Sleeve member 20 has an opening 22 on one side which is sized to permit the insertion of the test vial 18 when opening 22 and opening 17 are aligned. Smaller window openings 23 and 24 are provided on sleeve member 20 which are of insufficient size for removal of test vial 18. The base end of sleeve member 20 is provided with a plurality of openings 25 which are sized to fit over the boss or abutment 19.

In FIG. 3, the probe element 11 is shown with sleeve 20 rotated to align opening 22 with the opening 17 in the cylindrical portion 12 of the probe chamber element. Test vial 18 is shown in position in the test chamber 15. In FIG. 4, sleeve 20 has been rotated a one-half turn so that the opening 17 in chamber element 11 is obstructed. In this view, test vial 18 is shown in dotted position. Window openings 23 and 24 are shown in a position reversed from the view shown in FIG. 3 and are alignable in part with openings 19 in the test probe element.

OPERATION

While this invention should be easily understood from the foregoing description of the component parts, a brief description of operation will be given for clarification and further understanding.

When a body of biologically contaminated material 5 is placed in a steam autoclave 1, it has been difficult to determine whether the material has been thoroughly sterilized and biologically inactivated during treatment. The biological indicator probe 4 makes it possible to safely and effectively measure the steam sterilization of biologically contaminated material.

In using this system, a test vial 18 is placed in the chamber or pocket 15 of the test probe portion 11. Test vial 18 is inserted through the opening provided by the alignment of opening 22 in closure sleeve 20 and opening 17 into chamber or pocket 15. The sleeve 20 is then rotated one-half turn to secure test vial 18 in position. Test vial 18 is open to exposure to high temperature, pressurized steam through windows 23 and 24 and end opening 16.

The test probe is inserted into the material being treated. The conical tip 14 of the test probe 4 is inserted between bags or packages of the contaminated material or may, if desired, be inserted into one of the bags of packages. High temperature, pressurized steam is introduced into autoclave 1 and the contents of the autoclave held in contact with the high temperature steam for a time sufficient to inactivate the biologically contaminated materials.

The temperature in the autoclave is monitored by means of a temperature gauge connected to wires 10 leading from thermocouple 9. When a time has passed which is considered sufficient for the inactivation of the hazardous waste materials, the pressure is lowered to ambient in the sterilizer chamber and the chamber door 2 is opened. The test probe 4 is withdrawn from the autoclave and test vial 18 is removed from the test probe chamber element 11.

Test vial 18 which contains a standardized, test microorganism, is cultured to determine whether the test microorganism is still capable of reproduction. If the culture grows, it is evident that the culture has not been inactivated, which makes it likely that the contaminated materials have not been thoroughly inactivated and need further treatment. If a test culture does not grow, it is evidence of a thorough sterilization of the treated materials.

While this invention has been described fully and completely with emphasis on a single preferred embodiment, it should be understood that, within the scope of the appended claims, this invention may be practiced otherwise than as specifically described herein, e.g. the test probe may be used in ethylene oxide sterilization and other types of sterilization.

I claim:

1. A probe for use with biologically contaminated materials being subjected to a sterilizing environment comprising an elongated rod of heat resistant plastic material having a handle portion at one end and a test probe chamber element removably secured on the other end thereof, said test probe chamber element being of heat resistant plastic material and hollow to provide a chamber for receiving a biological test specimen vial and having an opening in the side wall thereof for insertion of a specimen vial, and a closure sleeve member rotatably positioned on said test probe chamber element and having an opening in the wall thereof of sufficient size for insertion of a specimen vial therethrough when rotated to align said test probe chamber element opening and said sleeve member opening and being rotatable to another position providing a closure for said test probe chamber element opening to retain a test specimen vial therein and having openings exposing a vial to a sterilizing environment.

2. A probe according to claim 1 in which
said rod, test probe chamber element and sleeve member are of a heat resistant thermoplastic or thermosetting plastic material.

3. A probe according to claim 2 in which
said heat resistant plastic material is a polysulfone or an epoxy plastic resin.

4. A probe according to claim 1 in which
the end of said test probe chamber element is tapered to facilitate insertion of said probe into a mass of material being biologically sterilized by steam heat.

5. A probe according to claim 1 in which
said test probe chamber element includes an abutment thereon, and
said sleeve member includes an opening engageable with said abutment for locking said sleeve member in an open or a closed position.

6. A probe according to claim 1 in which
said rod has a recess adjacent to said test probe chamber element, and
temperature measuring means supported in said rod recess operable to register the probe temperature.

7. A probe according to claim 6 in which
said rod recess includes a passage extending longitudinally for the length thereof,
said temperature measuring means comprises a thermocouple positioned in said recess having wires extending through said rod passage.

8. A probe according to claim 7 in which
said rod includes a plug connector insert in the end of the handle portion of said rod and connected to said wires.

9. A probe according to claim 7 in which
said rod recess comprises an aperture extending laterally through said rod adjacent to said probe chamber element and intersecting said longitudinal passage,
said thermocouple being positioned in said aperture and having wires extending through said longitudinal passage.

10. A probe according to claim 1 in which
said rod, test probe chamber element and sleeve are of a polysulfone resin, and
the end of said test probe chamber element is tapered to facilitate insertion of said probe into a mass of material being biologically sterilized by steam heat.

11. A probe according to claim 1 in which
said rod, test probe chamber element and sleeve member are of a polysulfone plastic,
the end of said test probe chamber element is tapered to facilitate insertion of said probe into a mass of material being biologically sterilized by steam heat,
said test chamber element includes an abutment thereon, and
said sleeve member includes an opening engageable with said abutment for locking said sleeve member in an open or a closed position.

12. A probe according to claim 1 in which
said rod, probe chamber element and sleeve member are of a polysulfone plastic,
the end of said test probe chamber element is tapered to facilitate insertion of said probe into a mass of material being biologically sterilized by steam heat,
said test probe chamber element includes an abutment thereon,
said sleeve member includes an opening engageable with said abutment for locking said sleeve member in an open or a closed position,
said rod has a recess adjacent to said test probe chamber element, and
temperature measuring means supported in said rod recess operable to register the probe temperature.

13. A probe according to claim 1 in which
said rod, probe chamber element and sleeve member are of a polysulfone plastic,
the end of said test probe chamber element is tapered to facilitate insertion of said probe into a mass of material being biologically sterilized by steam heat,
said probe chamber element includes an abutment thereon,
said sleeve member includes an opening engageable with said abutment for locking said sleeve member in an open or a closed position,
said rod has a recess adjacent to said test probe chamber element, and
temperature measuring means supported in said rod recess operable to register the probe temperature, and
said temperature measuring means comprising a thermocouple positioned in said recess having wires extending through said rod to a plug connector insert.

14. A biological indicator probe system comprising,
an elongated rod of heat resistant plastic material,
a test probe chamber element of non-metallic, heat resistant material removably secured in the end of said rod,
said test probe chamber element being of heat resistant plastic material and hollow to provide a chamber for receiving a biological test specimen vial and having an opening in the side wall thereof for insertion of a specimen vial,
a closure sleeve member rotatably positioned on said test probe chamber element and having an opening in the wall thereof of sufficient size for insertion of a specimen vial therethrough when rotated to align said test probe chamber element opening and said sleeve member opening and being rotatable to another position providing a closure for said test probe chamber element opening to retain a test specimen vial therein and having openings exposing a vial to a sterilizing environment, and
a tubular biological test specimen vial, containing biological material capable of inactivation at a selected temperature, positioned in said chamber to indicate the presence of conditions destructive of a biologically contaminated mass into which said probe is inserted during sterilization in a thermal autoclave.

15. A biological indicator probe system according to claim 14 in which said rod, test probe chamber element and sleeve member are of a heat resistant thermoplastic or thermosetting plastic material.

16. A biological indicator probe system according to claim 14 in which
said heat resistant plastic material is a polysulfone or an epoxy plastic resin.

17. A biological indicator probe system according to claim 14 in which
the end of said test probe chamber element is tapered to facilitate insertion of said probe into a mass of material being biologically sterilized by steam heat.

18. A biological indicator probe system according to claim 14 in which
said test probe chamber element includes an abutment thereon, and
said sleeve member includes an opening engageable with said abutment for locking said sleeve member in an open or a closed position.

19. A biological indicator probe system according to claim 14 in which
said rod has a recess adjacent to said test probe chamber element, and
temperature measuring means supported in said rod recess operable to register the probe temperature.

20. A biological indicator probe system according to claim 19 in which
said rod recess includes a passage extending longitudinally for the length thereof,
said temperature measuring means comprises a thermocouple positioned in said recess adjacent to said test probe chamber element having wires extending through said rod passage to a plug connector insert.

21. A biological indicator probe system according to claim 20 in which
said rod recess comprises an aperture extending laterally through said rod adjacent to said probe chamber element and intersecting said longitudinal passage,
said thermocouple being positioned in said aperture and having wires extending through said longitudinal passage.

* * * * *